United States Patent
Yanni et al.

(10) Patent No.: US 6,174,914 B1
(45) Date of Patent: Jan. 16, 2001

(54) METHOD OF INHIBITING CYTOKINE RELEASE FROM HUMAN OCULAR CELLS

(75) Inventors: John M. Yanni, Burleson; Daniel A. Gamache; Lori K. Weimer, both of Arlington, all of TX (US)

(73) Assignee: Alcon Laboratories, Inc., Fort Worth, TX (US)

( * ) Notice: Under 35 U.S.C. 154(b), the term of this patent shall be extended for 0 days.

(21) Appl. No.: 09/333,454

(22) Filed: Jun. 15, 1999

Related U.S. Application Data

(60) Provisional application No. 60/092,762, filed on Jul. 14, 1998.

(51) Int. Cl.$^7$ .................................................. A61K 31/335
(52) U.S. Cl. ............................................................... 514/450
(58) Field of Search ............................................... 514/450

(56) References Cited

U.S. PATENT DOCUMENTS

| | | | |
|---|---|---|---|
| 4,871,865 | 10/1989 | Lever, Jr. et al. | 549/354 |
| 4,923,892 | 5/1990 | Lever, Jr. et al. | 514/450 |
| 5,116,863 | 5/1992 | Oshima et al. | 514/450 |
| 5,641,805 | 6/1997 | Yanni et al. | 514/450 |

FOREIGN PATENT DOCUMENTS

| | | |
|---|---|---|
| 0 048 023 A2 | 3/1982 | (EP) . |
| 0 214 779 A1 | 3/1987 | (EP) . |
| 0 235 796 A2 | 9/1987 | (EP) . |

OTHER PUBLICATIONS

Yanni et al. (l), Ocul. Pharmacol. Ther., vol. 12, No. 4, pp. 389–400, 1996.*

Kamei et al, Biol. Pharm. Bull., vol. 18, No. 11, pp. 1518–1521, Nov. 1995.*

Kamei et al, Arzneimittelforschung, vol. 45, No. 9, pp. 1008–1008, Sep. 1995.*

Miki et al., "Histamine Enhanced the TNF–α–Induced Expression of E–Selectin and ICAM–1 on Vascular Endothelial Cells," *Cellular Immunology*, vol. 171, pp. 285–288 (1996).

Church, "Is Inhibition of Mast Cell Mediator Release Relevant to the Clinical Activity of Anti–allergic Drugs?," *Agents and Actions*, vol. 18, 3/4, pp. 288–293 (1986).

Clegg et al., "Histamine Secretion from Human Skin Slices Induced by Anti–IgE and Artificial Secretagogues and the Effects of Sodium Cromoglycate and Salbutanol," *Clin. Allergy*, vol. 15, pp. 321–328 (1985).

Hamilton et al., "Comparison of a New Antihistaminic and Antiallergic Compound KW 4679 with Terfenadine and Placebo on Skin and Nasal Provocation in Atopic Individuals," *Clinical and Experimental Allergy*, vol. 24, pp. 955–959 (1994).

Ikeda et al., "Effects of Oxatomide and KW–4679 on Acetylcholine–Induced Responses in the Isolated Acini of Guinea Pig Nasal Glands," *Int. Arch. Allergy Immunol.*, vol. 106, pp. 157–162 (1995.

Irani et al., "Mast Cell Heterogeneity," *Clinical and Experimental Allergy*, vol. 19, pp. 143–155 (1989).

Kamei et al., "Effects of Certain Antiallergic Drugs on Experimental Conjunctivitis in Guinea Pigs," Atarashii Ganka, vol. 11(4), p. 603–605 (1994) (abstract only).

Kamei et al., "Effect of (Z)–11–[3–(Dimethylamino) propylidene]–6,11–dihydrodibenz[b,e]oxepin–2–acetic Acid Hydrochloride on Experimental Allergic Conjunctivitis and Rhinitis in Rats and Guinea Pigs," *Arzneimittelforschung*, vol. 45 (9), p. 1005–1008 (1995).

Ohshima et al., "Synthesis and Antiallergic Activity of 11–(Aminoalkylidene)–6,11,dihydrodibenz[b,e] oxepin Derivatives," *J. Medicinal Chemistry*, vol. 35(11), p. 2074–2084 (1992).

Pearce et al., "Effect of Disodium Cromoglycate on Antigen Evoked Histamine Release in Human Skin," *Clinical Exp. Immunol.*, vol. 17, pp. 437–440 (1974).

Sharif et al., "Characterization of the Ocular Antiallergic and Antihistaminic Effects of Olopatadine (AL–4943A), a Novel Drug for Treating Ocular Allergic Diseases," *J. of Pharmacology and Experimental Therapeutics*, vol. 278(3), p. 1252–1261 (1996).

Sharif et al., "Olopatadine (AL–4943A): Pharmacological Profile of a Novel Anti–histaminic/Anti–allergic Drug for Use in Allergic Conjunctivitis," *Investigative Ophthalmology & Visual Science*, vol. 37(3), p. 1027 (1996) (abstract only).

Siraganian, "An Automated Continuous Flow System for the Extraction and Fluorometric Analysis of Histamine," *Anal. Biochem.*, vol. 57, pp. 383–394 (1974).

Spitalny et al., "Olopatadine Ophthalmic Solution Decreases Itching and Redness Associated with Allergic Conjunctivitis," *Investigative Ophthalmology & Visual Science*, vol. 37(3), p. 593 (1996) (abstract only).

Yanni et al., "The In Vitro and In Vivo Ocular Pharmacology of Olopatadine (AL–4943A), An Effective Anti–allergic/Anti–histaminic Agent," *Investigative Ophthalmology & Visual Science*, vol. 37(3), p. 1028 (1996) (abstract only).

Yoshida et al., "Role of NF–kB–Mediated Interleukin–8 Expression in Intraocular Neovascularization," Investigative Ophthalmology & Visual Science, vol. 39(7), pp. 1097–1106 (1998).

Zhang et al., "Optically Active Analogues of Ebastine: Synthesis and Effect of Chirality on Their Antihistaminic and Antimuscarinic Activity," *Chirality*, vol. 6(8), p. 631–641 (1994).

(List continued on next page.)

Primary Examiner—James H. Reamer
(74) Attorney, Agent, or Firm—Patrick M. Ryan

(57) ABSTRACT

Ophthalmic formulations containing as an active ingredient 11-(3-dimethylaminopropylidene)-6,11-dihydrodibenz[b,e]oxepin-2-acetic acid or a pharmaceutically acceptable salt thereof are useful for inhibiting cytokine release (e.g., IL-6 and IL-8) from human ocular cells. Such formulations can be used to treat or prevent ocular neovascularization and non-allergic inflammatory disorders such as dry-eye, keratitis, blepharitis, uveitis and inflammation related to infection.

14 Claims, No Drawings

OTHER PUBLICATIONS

"The Lung," *Scientific Foundations*, Raven Press, Ltd., New York, Ch. 3.4.11 (1991).

Cutarelli et al., "The Painful Eye External and Anteiror Segment Causes," *Clinics in Geriatric Medicine*, vol. 15 (1), pp. 103–112 (1999).

Yanni et al., "Inhibition of Histamine–Induced Human Conjunctival Epithelial Cell Responses by Ocular Allergy Drugs," *Arch. Ophthalmology*, vol. 117, pp. 643–647 (1999).

* cited by examiner

METHOD OF INHIBITING CYTOKINE RELEASE FROM HUMAN OCULAR CELLS

This application claims priority from co-pending U.S. Provisional Patent Application Ser. No. 60/092,762, filed Jul. 14, 1998.

BACKGROUND OF THE INVENTION

1. Field of the Invention

The present invention relates to ophthalmic pharmaceutical formulations. More particularly, the present invention relates to therapeutic and prophylactic use of 11-(3-dimethylamino-propylidene)-6,11-dihydrodibenz[b,e]oxepin-2-acetic acid for treating and/or preventing cytokine release from human ocular cells and resulting ocular neovascularization or non-allergic inflammatory conditions.

2. Description of the Related Art

As taught in U.S. Pat. Nos. 4,871,865 and 4,923,892, both assigned to Burroughs Wellcome Co. ("the Burroughs Wellcome Patents"), certain carboxylic acid derivatives of doxepin, including 11-(3-dimethylaminopropylidene)-6,11-dihydrodibenz[b,e]oxepine-2-carboxylic acid and 11-(3-dimethylamino-propylidene)-6,11-dihydrodibenz[b,e]oxepine-2(E)-acrylic acid, have antihistaminic and antiasthmatic activity. These two patents classify the carboxylic acid derivatives of doxepin as mast cell stabilizers with antihistaminic action because they are believed to inhibit the release of autacoids (i.e., histamine, serotonin, and the like) from mast cells and to inhibit directly histamine's effects on target tissues. The Burroughs Wellcome Patents teach various pharmaceutical formulations containing the carboxylic acid derivatives of doxepin; Example 8 (I) in both of the patents discloses an ophthalmic solution formulation.

U.S. Pat. No. 5,116,863, assigned to Kyowa Hakko Kogyo Co., Ltd., ("the Kyowa patent"), teaches that acetic acid derivatives of doxepin, including Z-11-(3-dimethylaminopropylidene)-6,11-dihydrodibenz[b,e]oxepin-2-acetic acid, have anti-allergic and anti-inflammatory activity. The anti-inflammatory activity is attributable to prostaglandin biosynthesis inhibiting activity (see Col. 28, lines 51–57). The doxepin derivatives disclosed by the Kyowa patent are represented by Compound (I):

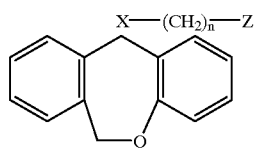

$$X\text{---}(CH_2)_{\overline{n}}\text{---}Z \quad (I)$$

Compounds where X represents =N—, =CH— or —CH$_2$— are described as having strong antiallergic activity, whereas compounds where X represents =N— are described as having strong antiinflammatory activity (see Col. 24, lines 20–57). Thus, for anti-inflammatory applications, the Kyowa patent suggests doxepin derivatives of Compound (I) where X is =N—.

The Kyowa patent demonstrates anti-allergic activity and anti-inflammatory activity in Wistar male rats. Medicament forms taught by the Kyowa patent for the acetic acid derivatives of doxepin include a wide range of acceptable carriers; however, only oral and injection administration forms are mentioned. In the treatment of allergic eye disease, such as allergic conjunctivitis, such administration methods require large doses of medicine.

U.S. Pat. No. 5,641,805 discloses topical ophthalmic formulations containing 11-(3-dimethylamino-propylidene)-6,11-dihydrodibenz[b,e]oxepin-2-acetic acid for treating allergic eye diseases.

SUMMARY OF THE INVENTION

The present invention provides a method for treating or preventing ophthalmic neovascularization and non-allergic inflammatory disorders involving cytokine release from human ocular cells. The method comprises inhibiting cytokine release from human ocular cells by administering to the eye an ophthalmic formulation which contains a therapeutically effective amount of 11-(3-dimethylaminopropylidene)-6,11-dihydrodibenz[b,e]oxepin-2-acetic acid (referred to as "Compound A" hereinafter) or a pharmaceutically acceptable salt thereof. The formulation may contain the cis isomer of Compound A (Z-11-(3-dimethylaminopropylidene)-6,11-dihydrodibenz-[b,e]oxepin-2-acetic acid), the trans isomer of Compound A (E-11-(3-dimethylaminopropylidene)-6,11-dihydrodibenz[b,e]oxepin-2-acetic acid), or a combination of both the cis and the trans isomers of Compound A. Unless specified otherwise, "11-(3-dimethylaminopropylidene)-6,11-dihydrodibenz-[b,e]oxepin-2-acetic acid" or "Compound A" means the cis isomer, the trans isomer or a mixture of both. "Cis isomer" means the cis isomer substantially free of the trans isomer; "trans isomer" means the trans isomer substantially free of the cis isomer. One isomer is "substantially free" of the other isomer if less than about two percent of the unwanted isomer is present.

DETAILED DESCRIPTION OF THE INVENTION

Compound A is a known compound and both the cis and the trans isomers of Compound A can be obtained by the methods disclosed in U.S. Pat. No. 5,116,863, the entire contents of which are hereby incorporated by reference in the present specification.

Examples of the pharmaceutically acceptable salts of Compound A include inorganic acid salts such as hydrochloride, hydrobromide, sulfate and phosphate; organic acid salts such as acetate, maleate, fumarate, tartrate and citrate; alkali metal salts such as sodium salt and potassium salt; alkaline earth metal salts such as magnesium salt and calcium salt; metal salts such as aluminum salt and zinc salt; and organic amine addition salts such as triethylamine addition salt (also known as tromethamine), morpholine addition salt and piperidine addition salt.

Compound A may be administered to the eye in a variety of ways. The most preferred way is by means of conventional topical ophthalmic formulations, such as solutions, suspensions or gels. Alternatively, Compound A may be administered to the eye via injection or implant. Depending upon the type of formulation, conventional ingredients will be combined with Compound A. The preferred formulation for topical ophthalmic administration of Compound A is a solution administered as eye drops. The preferred form of Compound A in the ophthalmic formulations of the present invention is the cis isomer. A general method of preparing an eye drop formulation of the present invention is described below as a nonlimiting example.

Compound A and an isotonic agent are added to sterilized purified water, and if required, a preservative, a buffering agent, a stabilizer, a viscous vehicle and the like are added to the solution and dissolved therein. The concentration of Compound A is 0.0001 to 5 w/v %, preferably 0.0001 to 0.001 w/v %, and most preferably about 0.0005 w/v %, based on the sterilized purified water. After dissolution, the pH is adjusted with a pH controller to be within a range suitable for use as an ophthalmic medicine, preferably within the range of 4.5 to 8.

Sodium chloride, glycerin, mannitol or the like may be used as the isotonic agent; p-hydroxybenzoic acid ester, benzalkonium chloride or the like as the preservative; sodium hydrogenphosphate, sodium dihydrogenphosphate, boric acid or the like as the buffering agent; sodium edetate or the like as the stabilizer; polyvinyl alcohol, polyvinyl pyrrolidone, polyacrylic acid or the like as the viscous vehicle; and sodium hydroxide, hydrochloric acid or the like as the pH controller.

If required, other ophthalmic drugs such as epinephrine, naphazoline hydrochloride, berberine chloride, sodium azulenesulfonate, lysozyme chloride, glycyrrhizate and the like may be added.

The eye drops produced by the above method typically need only be applied to the eyes a few times a day in an amount of one to several drops at a time, though in more severe cases the drops may be applied several times a day. A typical drop is about 30 µl.

According to the method of the present invention, ophthalmic formulations containing Compound A are used to inhibit pro-inflammatory cytokine secretion from human ocular cells, such as human conjunctival epithelial cells. This type of cytokine secretion (e.g., IL-6 and IL-8) can stimulate ocular neovascularization (see, for example, Yoshida et al., IOVS, 39:1097 (1998)) and other non-allergic inflammatory conditions, such as dry eye, keratitis, blepharitis, uveitis and inflammation related to infection, for example.

Certain embodiments of the invention are illustrated in the following examples.

EXAMPLE 1

Preferred Topical Ophthalmic Solution Formulation

| Ingredient | Concentration (W/V %) |
| --- | --- |
| Compound A•HCl | 0.111* |
| Dibasic Sodium Phosphate (Anhydrous), USP | 0.5 |
| Sodium Chloride, USP | 0.65 |
| Benzalkonium Chloride | 0.01 |
| Sodium Hydroxide, NF | q.s. pH = 7.0 |
| Hydrochloric Acid, NF | q.s. pH = 7.0 |
| Purified Water | q.s. 100 |

*0.111% Compound A•HCl is equivalent to 0.1% Compound A

EXAMPLE 2

Topical Ophthalmic Gel Formulation

| Ingredient | Concentration (W/V %) |
| --- | --- |
| Compound A•HCl | 0.11* |
| Carbopol 974 P | 0.8 |
| Disodium EDTA | 0.01 |
| Polysorbate 80 | 0.05 |
| Benzalkonium Chloride, Solution | 0.01 + 5 xs |
| Sodium Hydroxide | q.s. pH 7.2 |

| Ingredient | Concentration (W/V %) |
| --- | --- |
| Hydrochloric acid | q.s. pH 7.2 |
| Water for Injection | q.s. 100 |

*0.11% Compound A•HCl is equivalent to 0.1% Compound A

EXAMPLE 3

Inhibition of Cytokine Release

A. Human Conjunctival Epithelial Cell (HCE) Cultures.

Methods detailing the preparation of primary epithelial cell cultures and cytokine release studies using these cells have been described. See Gamache, et al., "Secretion of proinflammatory cytokines by human conjunctival epithelial cells," *Ocul Immunol Inflamm.*, 5:117–128 (1997). Briefly, cultures of human conjunctival epithelial cells were initiated from donor tissues obtained within eight hours post mortem by various eye banks. The tissues were enzymatically digested overnight. Epithelial cells were gently scraped from the tissue surface, dissociated into a single cell suspension, and cultured in keratinocyte growth medium (Clonetics®, San Diego, Calif.). Cells were used only through passage 6. Cultures were maintained in a preconfluent state to prevent differentiation. Cells were identified as epithelial by positive keratin staining.

B. Cytokine Assays.

Several compounds with histamine $H_1$ antagonist activity were evaluated for their ability to inhibit secretion of cytokines (IL-6 and IL-8) from cultured human conjunctival epithelial cells in response to histamine stimulation. Cells were plated at $2\times10^4$ cells/well and cultured overnight at 5% $CO_2$/37° C. The following day, fresh medium containing test compound was added directly to wells and the cells were incubated for 30 minutes prior to 24-hour stimulation with histamine (30 µM). Three separate culture wells were used for each treatment group. At harvest, supernatants were collected, centrifuged at 200× g, and stored at −20° C. Samples were analyzed for IL-6 and IL-8 by ELISA (R&D Systems, Minneapolis, Minn.) as directed by the manufacturer. The sensitivities of each ELISA are as follows: IL-6 0.7 pg/ml and IL-8 3.0 pg/ml.

C. Data Analysis

The antagonist potency ($IC_{50}$) was defined as the concentration of the drug required to produce 50% inhibition of the agonist-stimulated functional response. Data derived from the cytokine assays were calculated as mean and standard error (SEM) values which represent the variability among identically treated culture wells. The dose-dependent effect of pharmacological agents and $IC_{50}$'s were determined by linear regression. Data are expressed as mean ±S.E.M. from 3–5 independent experiments.

D. Results.

Exposure of HCE to 30 µM of histamine increased IL-6 and IL-8 secretion 1.59±0.19 and 1.80±0.28 fold above basal levels, respectively. (Basal levels of the cytokines were 153±42 pg/ml, n=4, for IL-6 and 197±48 pg/ml, n=6, for IL-8.)

Treatment of HCE with drugs possessing anti-histaminic activity and available for topical ocular administration prior to histamine exposure resulted in concentration-dependent inhibition of IL-6 secretion and IL-8 secretion. The results are shown below in Table 1.

The potency of emedastine in intact cells is consistent with its activity determined in receptor binding assays using tissue homogenates. Levocabastine also inhibited the IL-6, and IL-8 secretion at a level consistent with its $H_1$-receptor binding affinity. Antazoline and pheniramine, two first generation topical ocular anti-histamine compounds, were dramatically less potent inhibitors of IL-6 and IL-8 secretion than predicted from their histamine $H_1$-receptor binding affinities (20–140-fold). Olopatadine, however, was more potent than predicted from its published histamine $H_1$-receptor binding affinity (36 nM). Olopatadine, antazoline and pheniramine exhibit similar $H_1$ binding affinities (32–39 nM). Yet, olopatadine was approximately 10-fold more potent as an inhibitor of cytokine secretion ($IC_{50}$'s of 5.5 nM and 1.7 nM for IL-6 and IL-8 secretion, respectively) than predicted from binding data. These results indicate that, unlike the other compounds tested, olopatadine's ability to inhibit cytokine secretion is attributable to something more than $H_1$-receptor binding affinity.

TABLE 1

Histamine $H_1$ Antagonists: Inhibition of IL-6 and IL-8 Secretion in Human Conjunctival Epithelial Cells and $H_1$ Receptor Binding Affinities

| $H_1$ Antagonist | IL-6 $IC_{50}$ (nM) | IL-8 $IC_{50}$ (nM) | $H_1$ Binding $K_i$ (nM) |
| --- | --- | --- | --- |
| Emedastine[a] | 2.5 | 4.0 | 1.22* |
| Olopatadine[b] | 5.5 | 1.7 | 36.0 § |
| Levocabastine[c] | 25.1 | 11.9 | 52.6 * |
| Antazoline[d] | 1014 | 652 | 38.4 * |
| Pheniramine[e] | 4826 | 1216 | 33.9 * |

[a]1H-Benzimidazole,1-(2-ethoxyethyl)-2-(hexahydro-4-methyl-1H-1,4-diazepin-1-yl),(E)-2-butenedioate (1:2).
[b]Z-11-(3-Dimethylaminopropylidene)-6,11-dihydrodibenz
[c](-)-trans-1-[cis-4-Cyano-4-(p-fluorophenyl)cyclohexyl]-3-methyl-4-phenylisonipecotic acid monohydrochloride.
[d]4,5-Dihydro-N-phenyl-N-(phenylmethyl)-1H-imidazole-2-methanamine.
[e]N,N-Dimethyl-γ-phenyl-2-pyridine-propanamine.
* Sharif et al., J Ocul Pharmacol., 10:653–664 (1994)
§ Yanni et al., Ann Allergy Asthma Immunol., 79:541–545 (1997)

What is claimed is:

1. A method of treating or preventing ocular neovascularization and non-allergic ophthalmic inflammatory disorders involving cytokine release from human ocular cells comprising the step of administering to the eye a composition comprising a therapeutically-effective amount of 11-(3-dimethylaminopropylidene)-6,11-dihydrodibenz[b,e]oxepin-2-acetic acid or a pharmaceutically acceptable salt thereof.

2. The method of claim 1 wherein the composition is a topically administrable solution and the amount of 11-(3-dimethylaminopropylidene)-6,11-dihydrodibenz[b,e]oxepin-2-acetic acid is from about 0.0001 w/v.% to about 5% (w/v).

3. The method of claim 2 wherein the amount of 11-(3-dimethylaminopropylidene)-6,11-dihydrodibenz[b,e]oxepin-2-acetic acid is from about 0.0001 to about 0.001% (w/v).

4. The method of claim 3 wherein the amount of 11-(3-dimethylaminopropylidene)-6,11-dihydrodibenz[b,e]oxepin-2-acetic acid is about 0.0005% (w/v).

5. The method of claim 1 wherein the 11-(3-dimethylaminopropylidene)-6,11-dihydrodibenz[b,e]oxepin-2-acetic acid is (Z)-11-(3-dimethylaminopropylidene)-6,11-dihydrodibenz[b,e]oxepin-2-acetic acid, substantially free of (E)-11-(3-dimethylaminopropylidene)-6,11-dihydrodibenz[b,e]oxepin-2-acetic acid.

6. The method of claim 5 wherein the composition is a topically administrable solution and the amount of (Z)-11-(3-dimethylaminopropylidene)-6,11-dihydrodibenz[b,e]oxepin-2-acetic acid is from about 0.0001 to about 5% (w/v).

7. The method of claim 6 wherein the amount of (Z)-11-(3-dimethylaminopropylidene)-6,11-dihydrodibenz[b,e]oxepin-2-acetic acid is from about 0.0001 to about 0.001% (w/v).

8. The method of claim 7 wherein the amount of (Z)-11-(3-dimethylaminopropylidene)-6,11-dihydrodibenz[b,e]oxepin-2-acetic acid is 0.0005% (w/v).

9. The method of claim 1 wherein the 11-(3-dimethylaminopropylidene)-6,11-dihydrodibenz[b,e]oxepin-2-acetic acid is (E)-11-(3-dimethylaminopropylidene)-6,11-dihydrodibenz[b,e]oxepin-2-acetic acid, substantially free of (Z)-11-(3-dimethylaminopropylidene)-6,11-dihydrodibenz[b,e]oxepin-2-acetic acid.

10. The method of claim 9 wherein the composition is a topically administrable composition and the amount of (E)-11-(3-dimethylaminopropylidene)-6,11-dihydrodibenz[b,e]oxepin-2-acetic acid is from about 0.0001 to about 5% (w/v).

11. The method of claim 10 wherein the amount of (E)-11-(3-dimethylaminopropylidene)-6,11-dihydrodibenz[b,e]oxepin-2-acetic acid is from about 0.0001 to about 0.001% (w/v).

12. The method of claim 11 wherein the amount of (E)-11-(3-dimethylaminopropylidene)-6,11-dihydrodibenz[b,e]oxepin-2-acetic acid is about 0.0005% (w/v).

13. The method of claim 1 wherein the non-allergic ophthalmic inflammatory disorder is selected from the group consisting of dry eye, keratitits, blepharitis, uveitis and inflammation related to infection.

14. The method of claim 1 wherein the ocular neovascularization and non-allergic ophthalmic inflammatory disorders involve cytokine release from human conjunctival epithelial cells.

* * * * *